United States Patent [19]

Joslyn

[11] 4,115,068

[45] Sep. 19, 1978

[54] AIR DETECTING DEVICE FOR STEAM OR GAS STERILIZERS

[75] Inventor: Larry James Joslyn, Walworth, N.Y.

[73] Assignee: Sybron Corporation, Rochester, N.Y.

[21] Appl. No.: 785,093

[22] Filed: Apr. 6, 1977

[51] Int. Cl.² .................. A61L 3/02; G01N 25/00; G01N 31/22
[52] U.S. Cl. .................................... 422/56; 73/356; 116/114 V; 422/59; 422/87; 422/295
[58] Field of Search ............ 23/253 R, 232 R, 254 R; 21/94, 56, 95, 96, 97, 98, 103; 116/114 V; 73/356

[56] References Cited

U.S. PATENT DOCUMENTS

| | | | |
|---|---|---|---|
| 2,826,073 | 3/1958 | Huyck et al. | 116/114 V |
| 3,402,991 | 9/1968 | Hanfrey | 21/94 |
| 3,450,489 | 6/1969 | Fay | 21/94 X |
| 3,479,131 | 11/1969 | Scoffield et al. | 21/56 X |
| 3,667,916 | 6/1972 | Sliva et al. | 116/114 V X |
| 3,696,675 | 10/1972 | Gilmour | 116/114 V X |
| 3,769,932 | 11/1973 | Romito et al. | 116/114 V |
| 3,967,494 | 7/1976 | Joslyn | 21/56 X |

FOREIGN PATENT DOCUMENTS 1,143,343  2/1969  United Kingdom ................. 23/232 R Primary Examiner—Morris O. Wolk
Assistant Examiner—Arnold Turk
Attorney, Agent, or Firm—Theodore B. Roessel; Roger Aceto

[57] ABSTRACT

Air indicating device for use in steam or gas sterilizers and the like includes an upright tube placed in the sterilizer. The tube is open at its bottom to the sterilizing chamber and is closed at its top. A heat sink within the tube causes steam entering the tube to condense with a resulting accumulation of air in the top of the tube. The air accumulation acts as a barrier preventing further steam from reaching the upper portion of the tube. A temperature sensitive indicator strip extending axially into the tube changes color responsive to temperature. The air barrier is also an insulator so that the color of the indicator is a record of the temperature gradient from the top to the bottom of the tube, the temperature, in turn, being a measure of the amount of air trapped in the tube.

10 Claims, 2 Drawing Figures

AIR DETECTING DEVICE FOR STEAM OR GAS STERILIZERS

BACKGROUND OF THE INVENTION

The present invention relates to an indicator device which measures and makes a permanent record of the operational efficiency of a steam or gas sterilizer and in particular of the amount of residual air present in the sterilizer during a typical cycle of operation.

In steam sterilizing, it is well recognized that the ability to sterilize depends in large part on the adequate removal of air from the sterilizing chamber. For this reason a typical cycle involves the evacuation by one means or another of air prior to the admission of the sterilizing steam. Particularly when porous goods are being steam sterilized, any air in the goods acts as a barrier to the penetration of steam to the center of the goods and consequently, they will not be sterilized.

The usual method to insure that the sterilizer reduces air to an acceptable level is to periodically run a test cycle. The load utilized in the test cycle is a fairly standard test pack made up of porous goods such as linens and the like. Included in the pack is a spore strip which is incubated after the pack has been sterilized. If, after incubation the spore strip shows no bacteria growth, it is assumed that the sterilizer is operating properly. The drawback of such a test procedure is that the size of the test pack precludes the running of both the test load and an ordinary load at the same time so that while the test load is being run, the sterilizer is not available for normal use. Also, since the test load is run alone, there is no assurance that the sterilizer is operating properly between test loads.

There are devices available for continually monitoring the amount of air in the sterilizing chamber. Such devices typically monitor the environment within the sterilizing chamber by continuously bleeding a sample of the steam and entrapped air from the sterilizing chamber and analyzing this sample to determine its air content. Typical of such devices are illustrated in U.S. Pat. Nos. 3,402,991, 3,479,131 and 3,967,494. Such devices have the disadvantage of requiring special connections to the sterilizing chamber which themselves may become sources of air leaking into the sterilizing chamber when the chamber is evaluated.

The indicating device of the present invention requires no connection of exterior piping to the sterilizing chamber or a special test load. Instead, the indicator of the present invention may be placed into the sterilizing chamber along with the goods to be sterilized. The device requires a minimum of preparation and can provide a permanent record of each sterilizing cycle to show the amount of air, if any, in the chamber during the sterilizing cycle.

In sterilizing with a gas such as ethylene oxide, steam is often used to condition the goods prior to exposure to gas, the steam acting both to heat and moisturize the goods. Here residual air can also present problems so in another form, the present invention would have application to gas sterilizing cycles.

SUMMARY OF THE INVENTION

The present invention may be characterized in one aspect thereof by the provision of an upright tube adapted to be placed within a sterilizer, the tube defining an elongated chamber which is closed at its top and open at its bottom to the environment within the sterilizer; a heat sink within the chamber; and a thermal indicator strip extending axially into the chamber for substantially the full height thereof, the strip being impregnated with a chemical that undergoes a permanent color change upon the attainment of a predetermined temperature.

With the foregoing arrangement, the steam component of any air-stream mixture entering the tube chamber from the sterilizer is condensed, leaving a quantity of air at the top of the chamber. This air acts as a barrier to the penetration of steam to the top of the tube chamber and consequently the top of the chamber will be at a slightly cooler temperature than the lower part of the tube chamber. Since the strip in the tube chamber is temperature sensitive, a color change will occur at some point along the length of the thermal strip which corresponds generally to the point of penetration of the steam into the tube chamber. The length of the strip not undergoing a color change can be directly correlated to the amount of air present in the sterilizer during the sterilizing process.

DESCRIPTION OF THE PREFERRED EMBODIMENTS

Figure 1:
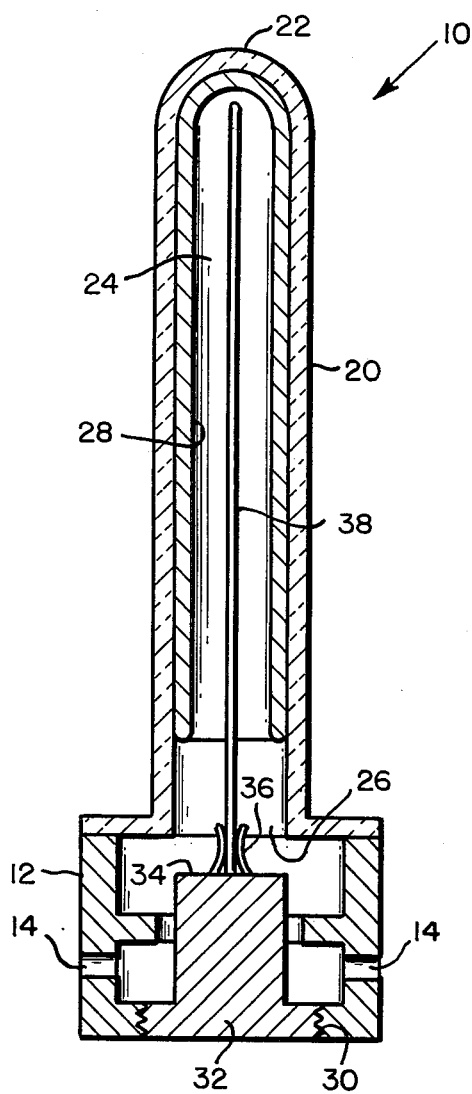
FIG. 1 is an elevation view in cross section of the air detecting device of the present invention for use in steam sterilization.

Referring to the drawings, FIG. 1 shows the air detecting device of the present invention generally indicated at 10 as may be used in steam sterilization. The device can be assembled and placed directly into a sterilizing chamber (not shown) along with the load of goods to be sterilized. The device 10 includes a base portion 12 which has an internal passage 14 open to the environment within the sterilizer.

Upstanding from the base member is a tubular portion 20 which is closed at its upper end 22. The upright tubular portion thus defines an elongated chamber 24 which is closed at the top and in open communication at its bottom 26 with the internal passage 14. Accordingly, chamber 24 is also open to the environment within the sterilizer. Both the base 12 and upright tubular portion 20 are preferably made of heat insulating material or at least have their outer surfaces provided with a heat insulating material. Lining the interior surface of tubular portion 20 is a heat sink 28 made of any suitable heat conducting material.

Releasably connected to base member 12, as by threads 30, is a plug 32. The plug extends into the base member and presents one end face 34 in axial alignment with the elongated chamber 24. This end face carries a clamp means such as the spring wire clips 36 as shown. These clips releasably support one end of a thermal indicator strip 38 which extends axially into chamber 24 for substantially the full height of the chamber.

Thermal strip 38 can be any of the thermal indicators well known in the art. These indicators are usually made from a paper stock and are either coated or impregnated with a known chemical that undergoes a permanent color change responsive to a predetermined temperature level. The entire length of the thermal strip is so coated so that it is possible to form a record of the temperature gradient along the full height of chamber 24 or at least to determine at what height into the chamber a particular temperature level is reached.

In operation, the indicator device 10 is prepared by first assembling the device which involves the simple procedure of attaching a thermal strip 38 between spring clips 36. The plug 32 is and then threaded into base portion 12 so as to locate the thermal strip in chamber 24. The assembled indicating device is then placed, in the upright position as shown, into a stream sterilizer along with a typical load to be sterilized.

Preferably, a number of such devices are placed at various locations in the sterilizer.

During a typical sterilizing cycle, the sterilizer is first evacuated which reduces the air in the sterilizer to a low level. Since chamber 24 is open to the sterilizer, the evacuation also reduces the air in chamber 24 to a low level. Next, steam is admitted to the sterilizer. As steam enters through open passage way 14 and into chamber 24, it comes in contact with heat sink 28 and condenses. The condensed steam drains back into the base portion. Any air remaining after evacuation or which had been mixed with the steam becomes trapped and accumulates to form an air pocket at the top of chamber 24. The accumulation of air at the top of chamber 24 acts as a barrier preventing steam from reaching the upper portion of the chamber and acts as a heat insulator for the thermal strip. In this respect, steam cannot penetrate the air barrier so that the portion of indicator strip 38 in the air pocket is at a lower temperature than the portion of the strip below the pocket. Since strip 38 is temperature sensitive, this temperature gradient will be recorded by the strip for measurement after the sterilizing cycle is complete.

Note that if all but a trace of air is removed from the sterilizer during the evacuation step, thermal indicator strip 38 would display an even temperature along its length to indicate sufficient air removal for sterilization. If insufficient air has been removed, the thermal indicator strip would display a color change at some point along its length, the position of the change being an indication of the amount of air in chamber 24.

The amount of steam which is collapsed by the device can be controlled in several ways. For example, the size of the upright portion 20 defining the volume of chamber 24 and the size of heat sink 28 can be controlled or the device can be cooled to a predetermined temperature prior to its placement in the sterilizer. Also it is possible to provide the heat sink with liquid filled areas (not shown) so as to increase the specific heat of the heat sink. In any event, it should be evident that the amount of air in the chamber (which is, in part, a function of the amount of steam collapsed and the amount of air remaining after evacuation) can be determined by correlating the temperature gradient indication on strip 38 to the volume of chamber 24.

Observing the strip upon completion of a sterilizing cycle and noting at what point along the strip a color change occurs, will give an immediate indication of whether sufficient air was removed for proper sterilization. As an added assurance of proper sterilization, the strip can be impregnated with a suitable bacterial spore (as is known in the art) prior to use and then incubated after use.

In the case of sterilization with a gas such as ethylene oxide, a typical cycle would consist of a load conditioning phase and an exposure phase. During the conditioning phase air is drawn from the sterilizing chamber. This can be accomplished by a simple evacuating system or by sweeping the air from the sterilizers by simultaneously introducing and evacuating steam. Steam or water vapor can then be introduced into the sterilizing chamber to heat and humdify the load in preparation for exposure to the gas. If air is not adequately removed from the chamber during the conditioning phase the same air barrier as in steam sterilizing is set up which prevents the proper humidification of the goods and the subsequent penetration of the sterilant gas to all parts of the load. The net result is that the cycle time is greatly dependant upon the amount of residual air in the sterilizing chamber. Accordingly, as with the steam sterilization, it is also important to monitor the residual air during gas sterilization. However, in order to insure that the indicator strip gives an accurate reading of the amount of air remaining in the sterilizer after the conditioning phase, the heating of the strip must stop prior to full pressurization with gas. Otherwise, the gas pressure would further compress the air in the tube. This, and the increase in temperature caused by pressurizing the sterilizer with gas would result in an inaccurate determination of the amount of residual air.

Figure 2:
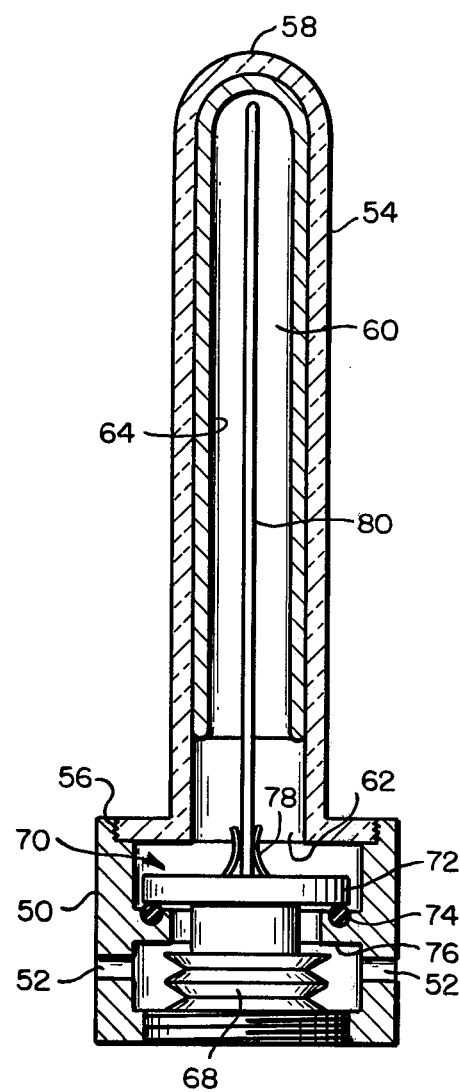
FIG. 2 is a view similar to FIG. 1 only showing an embodiment of the invention for use in gas sterilization.

For this reason a slight modification of the invention is required to adapt the air detecting device for use in gas sterilizers as will be seen by referring to the embodiment shown in FIG. 2. As in FIG. 1, the air detecting device includes a base 50 which is open to the environment within the sterilizer (not shown) through a passage 52.

Upstanding from this base is a tubular member 54 which is releasably attached to the base by any suitable means such as threads 56. The tubular member is closed at its upper end 58, so as to define a chamber 60 closed at the top and in open communication through its bottom 62 with the interior of base 50. The base and tubular member are preferably of a heat insulating material with the interior of the tubular member being lined with a heat sink 64.

Disposed in the base is a bellows 68 which operates a valve generally indicated at 70 formed by a sealing member 72 on the bellows and a gasket 74 disposed between the sealing member and an internal flange 76 of the base 50.

Completing the structure is a clamp means 78 on the sealing member. This clamp means supports a thermal indicator strip 80 which extends axially into chamber 60.

In operation, bellows 68 is evacuated during assembly and the components of valve 70 are sized in such a way that the sealing member 72 will remain seated against gasket 74 above some predetermined pressure. For example, a pressure of 2.54 psia will be used. Above this pressure then, valve 70 is closed and chamber 60 is sealed from the environment of the sterilizer. The closed position illustrated in FIG. 2 would now be the condition of the device at atmospheric pressure when it is placed into the sterilzer.

As the sterilizer evacuated and the external pressure on the bellows falls below the internal bellows pressure of 2.54 psia, the bellows will expand so as to unseat the sealing member 72 from gasket 7. This opens chamber 60 and allows air to be evacuated from the chamber as the sterilizer is evacuated.

During the moisturizing phase steam is introduced into the sterilizer in a manner which does not increase the pressure on the bellows. The internal pressure of the bellows will allow the valve to remain open so that steam will enter through passages 52 and around valve 70 into chamber 60. There, as in the embodiment of FIG. 1, the steam loses heat to heat sink 64 and condenses.

After the conditioning phase, the ethylene gas is introduced into the chamber at a pressure above the internal bellows pressure of 2.54 psia. This causes the bellows to collapse and close valve 70 thereby sealing chamber 60 from the environment of the sterilizer.

With chamber 60 sealed, the temperature gradient on the indicator strip will relate to the sterilizer air content during the conditioning phase and therefore will relate directly to the exposure time required for non-hermetrically sealed items. This provides an indication at the end of a cycle of whether the load has been properly preconditioned. In this respect, after removal from the sterilizer tubular member 54 is simply unthreaded from base 50 to observe the color change or color gradient along thermal strip 80.

Thus, it should be appreciated that the present invention accomplishes its intended objects in providing a simple, easily used device for accurately and quickly determining whether or not sufficient air has been removed from the sterilizer to permit sterilization. The device needs no plumbing or other connections to the sterilizer and instead is placed directly into the sterilizer. Inspection of the device when the sterilizing cycle is complete will give an immediate indication of whether sterility has occurred.

Having thus described the invention in detail what is claimed as new is:

1. An air detecting device for sterilizers and the like comprising:
   (a) an upright tube of heat insulating material, said tube having a closed top and an open bottom and defining an elongated chamber, said tube being adapted to be placed within a sterilizer so as to put said chamber in communication with the environment within the sterilizer through the open bottom of said upright tube;
   (b) a heat sink within said chamber for condensing at least part of any steam entering said chamber through the open bottom of said tube, the steam in said chamber condensed by said heat sink falling by gravity back through said tube while any air entrained with the steam entering said chamber becomes entrapped in and provides a heat insulator in said chamber adjacent the closed top of said tube thereby establishing a lower temperature adjacent the top of said tube than adjacent the bottom of said tube;
   (c) a thermal indicator strip in said chamber spaced from said heat sink;
   (d) means for supporting said thermal indicator strip whereby said strip extends from the open bottom to the closed top of said tube so that said strip extends substantially the full height of said chamber; and
   (e) said thermal indicator strip being temperature sensitive so as to undergo a permanent color change responsive to the temperature within said chamber to provide a record of the temperature from the top to the bottom of said chamber, said temperature being directly correlated to the amount of air entrapped adjacent the top of said chamber.

2. An air detecting device as in claim 1 wherein said heat sink lines substantially the entire internal surface of said tube.

3. An air detecting device as in claim 1 wherein said thermal strip is impregnated along the length with a bacterial spore.

4. Air detecting device as in claim 1, wherein said tube upstands from a base member, said base member having an open passage extending therethrough and communicating with said chamber and a removable portion, said means for supporting said thermal strip being connected to said removable portion.

5. An air detecting device as in claim 4 wherein said removable portion is a plug threaded through said base, said means for supporting said thermal strip being on an end face of said plug.

6. An air detecting device as in claim 5 wherein said means for supporting said thermal strip removably mounts said strip.

7. An air detecting device as in claim 5 wherein said means for supporting said thermal strip comprises spring wire clips on said end face, said thermal strip being releasably captured between said spring wire clips.

8. An air detecting device for use in sterilizers comprising:
   (a) a base having an open passage therethrough;
   (b) a tube portion of heat insulating material upstanding from said base, said tube defining an elongated chamber communicating at its lower end with said passage and closed at its top;
   (c) a heat sink lining the interior of said tube portion;
   (d) a removable plug member extending into said base, said plug having an end face in alignment with said elongated chamber;
   (e) clamp means on said end face; and
   (f) heat indicated means in said chamber supported by said clamp means, said heat indicating means being spaced from said heat sink and extending into said chamber for substantially the full height thereof and said heat indicating means being of a type which undergoes a permanent color change responsive to the temperature in said chamber.

9. An air detecting device as in claim 8 including a pressure operated valve means in said base for closing said elongated chamber above a predetermined pressure.

10. An air detecting device as in claim 9 wherein said pressure operated valve means comprises:
   (a) a bellows in said base, said bellows being evacuated to a predetermined pressure;
   (b) a chamber sealing member on said bellows, said bellows expanding and collapsing responsive to external pressure on said bellows to move said chamber sealing member between an open and closed position.

* * * * *